United States Patent [19]

Weinstein

[11] Patent Number: 5,217,005
[45] Date of Patent: Jun. 8, 1993

[54] APPARATUS FOR PERFORMING PERCUTANEOUS TRACHEOSTOMIES AND CRICOTHYROIDECTOMIES

[76] Inventor: James D. Weinstein, 1109 Woodland Dr., Bridgeport, W. Va. 26330

[21] Appl. No.: 786,729

[22] Filed: Nov. 1, 1991

[51] Int. Cl.5 .................................... A61M 16/00
[52] U.S. Cl. ..................... 128/200.26; 128/207.14; 128/207.29
[58] Field of Search ............... 128/200.26, 207.14, 128/207.15, 207.29

[56] References Cited

U.S. PATENT DOCUMENTS

| 2,991,787 | 7/1961 | Shelden et al. | 128/207.29 |
|---|---|---|---|
| 3,384,087 | 5/1968 | Brummelkamp | 128/207.29 |
| 4,246,897 | 1/1981 | Mato | 128/207.29 |
| 4,364,391 | 12/1982 | Toye | 128/207.29 |
| 4,471,778 | 9/1984 | Toye | 128/207.29 |
| 4,488,545 | 12/1984 | Shen | 128/207.29 |
| 4,520,810 | 6/1985 | Weiss | 128/207.29 |
| 4,677,978 | 7/1987 | Melker | 128/207.29 |
| 4,978,334 | 12/1990 | Toye et al. | 604/51 |
| 5,055,107 | 10/1991 | Lester | 128/207.29 |

Primary Examiner—Edgar S. Burr
Assistant Examiner—Aaron J. Lewis
Attorney, Agent, or Firm—Cindrich & Titus

[57] ABSTRACT

A percutaneous device for performing tracheostomies or cricothyroidectomies having a hollow needle with a sharp distal end. The device includes a flexible dilator slidably positioned over the needle. The dilator includes a conical portion and an annular groove, the apex of which is positioned adjacent the distal end of the needle and the base thereby terminating at the annular groove. A flexible breathing tube is slidably positioned over the dilator for insertion into a trachea or larynx.

6 Claims, 3 Drawing Sheets

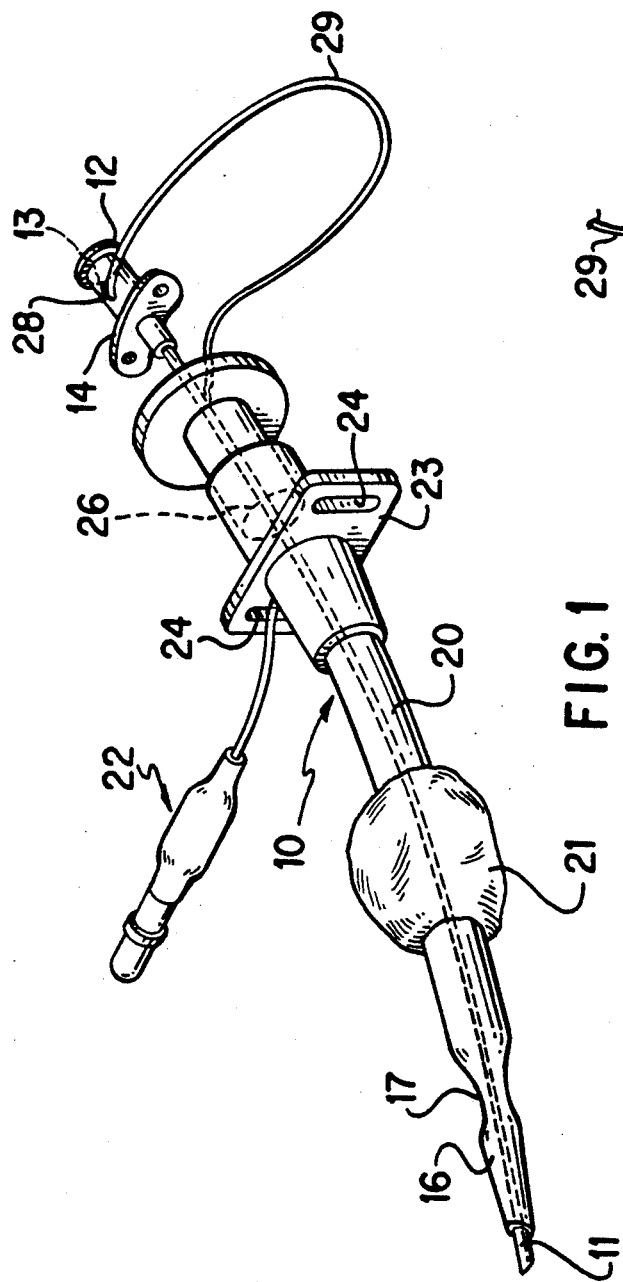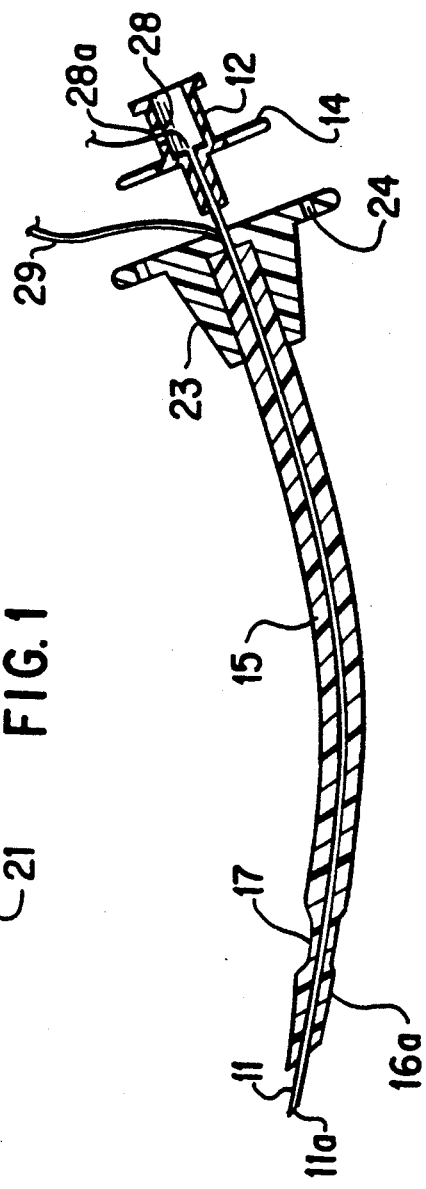

APPARATUS FOR PERFORMING PERCUTANEOUS TRACHEOSTOMIES AND CRICOTHYROIDECTOMIES

FIELD OF THE INVENTION

The present invention relates to apparatus for performing percutaneous tracheostomies and cricothyroidectomies and, in particular, to an improvement in such apparatus comprising an improved dilator portion which positively positions the dilator within the lumen and resides accidental removal therefrom.

BACKGROUND OF THE INVENTION

In performing a tracheostomy, it is generally necessary to perform a dissection for insertion of a breathing tube into the trachea. However, it is preferable to perform such tracheostomies utilizing devices which do not require surgical skill to perform the dissection. Apparatus has been developed to avoid the dissection procedures, including U.S. Pat. Nos. 3,511,243, 4,364,391 and 4,471,778. See also U.S. Pat. Nos. 4,699,611 and 5,009,643.

In the U.S. Pat. No. 4,978,334, a device is described which utilizes a single needle attached to a syringe having a dilator coaxially mounted therewith. Coaxially mounted around the dilator is a breathing tube. To perform a percutaneous tracheostomy with such a device, the needle is inserted into the lumen and the syringe plunger is withdrawn to confirm proper location of the needle. Upon confirmation of the needle location, the dilator is coaxially moved over the needle and into the lumen to serve as a flexible leader for the breathing tube. The coaxial arrangement of the dilator and breathing tube permits the removal of the dilator from the trachea leaving the breathing tube in place.

Notwithstanding the advantages of the apparatus disclosed in U.S. Pat. No. 4,978,334, it continues to be difficult to perform a percutaneous insertion of the needle and dilator so as to avoid passage of the device through the lumen into the walls and surrounding tissue thereof. Also, upon removal of the syringe and needle from the dilator, it is not abnormal to also pull the dilator out of position. Without the notch the dilator is relatively rigid and now likely to perforate the lumen wall, especially if the needle is not removed. Provision for a guide wire is not made with this invention. Accordingly, it is an object of the present invention to provide a device for percutaneous tracheostomy and/or cricothyroidectomy which overcomes prior art limitations. In particular, it is an object of this invention to provide a percutaneous device in which the dilator provides an indication of proper location in the lumen and resists accidental removal.

SUMMARY OF THE INVENTION

The present invention comprises a percutaneous device for performing tracheostomies or cricothyroidectomies. Generally, the device includes a hollow needle adapted for connection with a syringe. At its distal end the needle is formed with a sharp edge to penetrate the skin and tissue surrounding the trachea or larynx. The needle is used to percutaneously insert the device into the appropriate lumen. By attaching a syringe to the luer type fitting on the end of the needle, it is possible to confirm the fact that it has been inserted into the trachea or larynx by withdrawing the syringe plunger. If properly located, air should be withdrawn into the body of the syringe. If the tip is not within the air containing cavity (trachea) a vacuum effect will be noted on attempt at withdrawing the syringe plunger.

Coaxially positioned about the needle is a flexible dilator. The dilator includes an annular support flange for slidably moving the dilator coaxially over the needle or removing the dilator from a breathing tube as below. The dilator is provided with a conical portion at its distal end juxtapositioned so that its apex is adjacent to the distal end of the needle. Preferably, the height on the conical section is about one-half the average anterior/posterior diameter of the larynx or trachea. An annular groove or notch is provided at the base or terminus of the conical portion of the dilator whose function is the proper positioning of the device within the lumen. The conical shape of the distal end of the dilator creates a detectable resistance to its insertion through the tracheal or cricothyroid membranes and cartilage. This resistance abruptly changes upon reaching the notch in the dilator to provide a sensory indication to the user that the distal portion of the dilator and the needle are properly located within the trachea. When properly positioned, the elastic properties of the wall of the trachea tend to allow these tissues to "grasp" the notch section of the dilator and hold it in the proper position while air testing and guide wire insertion are performed.

Coaxially positioned over the dilator is an overlying breathing tube. After the guide wire is inserted down the airway, the needle tip is withdrawn into the dilator, past the notch. This allows the conical tip to become flexible, so as not to penetrate the tracheal wall with the subsequent insertion of the whole apparatus, (dilator and tube). The notch at the end of the conical tip of the dilator, being "held" by the wall elasticity of the trachea, resists being pulled out as the needle is withdrawn up into the dilator. After the whole device is placed within the trachea, the dilator and contained guide wire and needle are removed, leaving the functioning breathing tube in place.

Advantages of the apparatus of the present invention with a conical tip and adjacent notch are:

(1) length designed to place tip in middle of trachea upon insertion, (2) dilator held in place by elasticity of tracheal wall while air testing and guide wire insertion are done.

(3) allows change in the insertional resistance so as to have unit "stop" for air testing and guide wire insertion.

(4) tip becomes flexible with the withdrawal of needle past notch up dilator, so as to not allow perforation of wall of trachea with subsequent full insertion of the remainder of dilator and air tube.

The guide wire design is unique in that it allows the person inserting the unit to maintain touch and control of the apparatus while drawing air and then pushing in the guide wire. It is not necessary to pick up a separate piece, thereby releasing the unit partially within trachea. Other advantages of the invention will become apparent from a perusal of the following detailed description taken in connection with the accompanying drawings.

BRIEF DESCRIPTION OF DRAWINGS

FIG. 1 is a perspective view of the apparatus of the present invention;

FIG. 2 is a sectional elevation of the dilator and needle of the present invention.

PRESENTLY PREFERRED EMBODIMENT OF THE INVENTION

Figure 3:
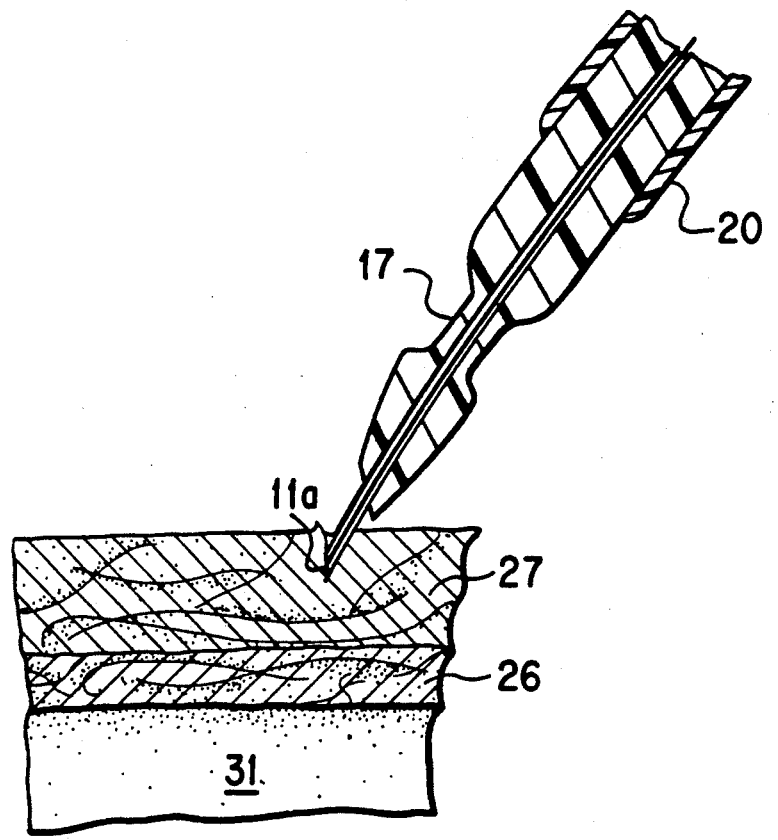
FIG. 3-6 are sectional elevations showing insertion of the apparatus of the present invention into a trachea lumen.

With reference to FIGS. 1 and 2, device 10, the present invention will be described with respect to its application in performing a percutaneous tracheostomy. Percutaneous device 10 includes an elongated hollow needle 11 having a sharpened distal end and 11a to penetrate the membranes and cartilage surrounding the trachea. Needle 11 terminates at its other end with a luer type fitting 12 having an opening 13 for communication with a syringe (not shown), fitting 12 includes handle 14 to facilitate removal of needle 11. In one embodiment of the invention, a syringe is used upon penetration of the tracheal lumen to confirm proper position within the trachea of the needle. By withdrawing the syringe plunger, air should enter the syringe if the needle is properly positioned.

Coaxially overlying needle 11 is dilator 15. Dilator 15 is preferably made from a Teflon ® tubular material. Distal end 16 of dilator 15 includes a conical portion 16a having an increasing radius and terminating in annular groove or notch 17. At its other end, dilator 15 includes annular flange 18 which provides a means for holding device 10 and for removing dilator 15 from the trachea. The height of conical portion 16a is preferably one-half the average anterior/posterior diameter of the larynx or trachea so as to properly locate the dilator. This height can be varied to accommodate children or patients with smaller body sizes to prevent the dilator from passing through the opposite wall of the lumen. Coaxially positioned over dilator 15 is breathing tube 20. Breathing tube 20 includes a bladder 21 for inflation within the trachea. Bladder 21 includes connector means 22 to a source of air pressure. Stop means 23 is provided at one end of tube 20. Stop means 23 also includes slots 24 for positioning the breathing tube to the neck of the patient using straps (not shown). Annular fitting 25 is provided to stop means 23 and in communication with tube 20 for connecting with a breathing apparatus (not shown).

Figure 4:
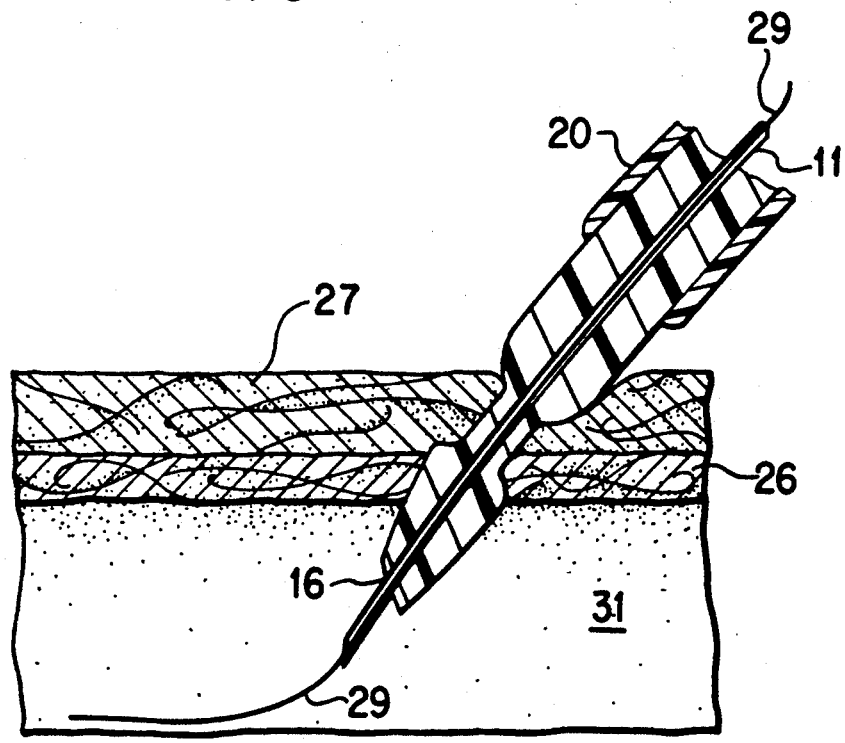

Referring to FIG. 3-6, in performing a tracheostomy, percutaneous device 10 is directed into the outer layers of cartilage and membrane 27 and trachea wall 26 by pressing the distal end 11a of needle 11 into skin through layer 27 and 26. During insertion, pressure is placed on needle 11 while holding annular flange 18 and stop means 23 and needle fitting 12. Typically, two "pops" are felt upon insertion; the first is needle 11 entering lumen 31 and the second is conical portion 16 of dilator 15 entering the lumen. The second pop is felt when groove 17 enters lumen 31 as shown in FIG. 4. At this point, a test is made for air flow by drawing on the syringe (not shown). Resistance and vacuum effect indicate that needle tip 11a is not in the lumen. However, when a good air return is obtained, the needle and dilator are properly positioned. As shown in FIG. 4, the needle is properly located within the lumen and the guide wire 29 has been inserted.

Figure 5:
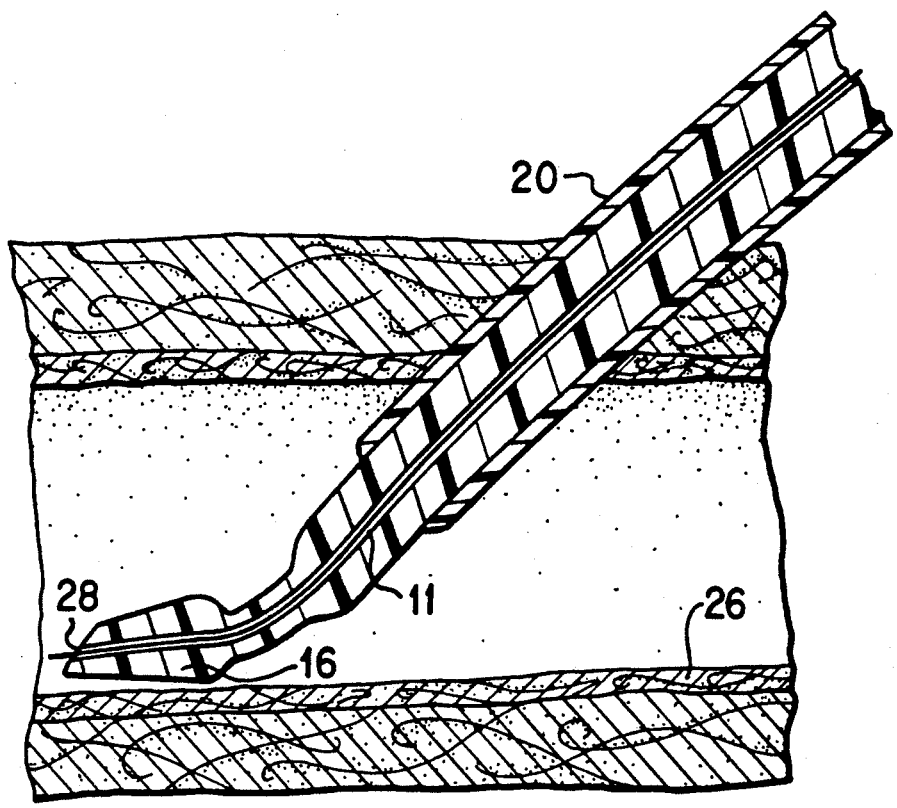
Figure 6:
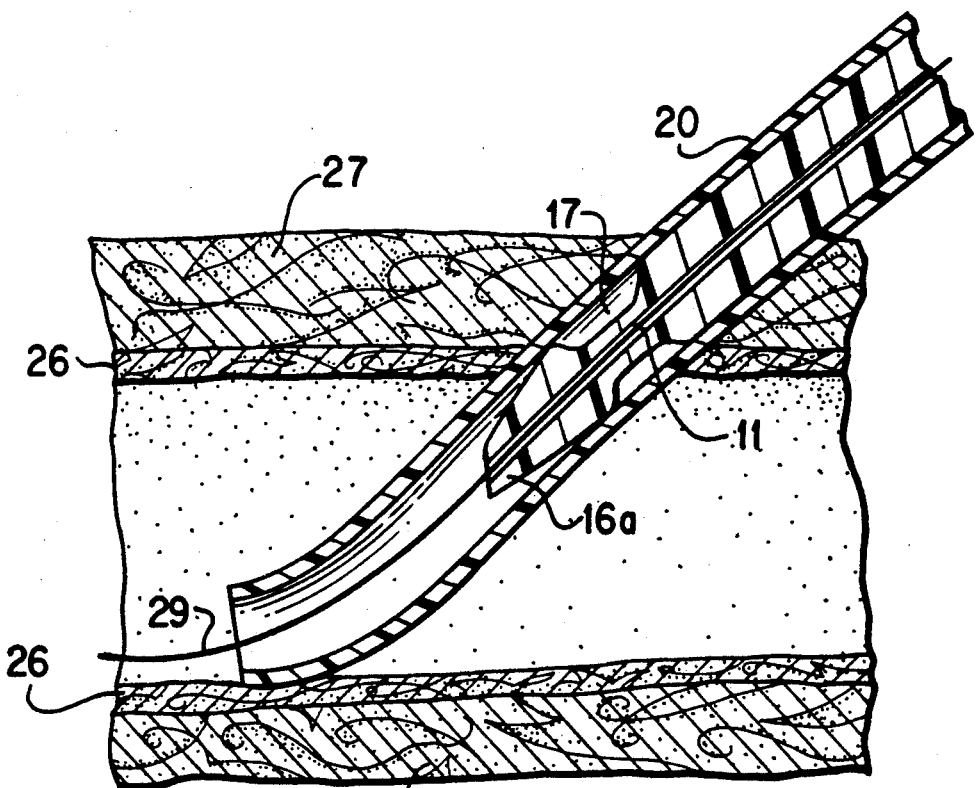

After positioning conical portion 16 in lumen 31 as shown in FIG. 4, needle 11 is withdrawn or removed from lumen 31 by use of handle 14. The annular groove 17 assists in preventing the distal end of dilator 15 from being prematurely or accidentally removed from the trachea. Upon withdrawal of needle 11, dilator 15 is inserted further into the lumen so that conical portion 16 bends and rests against the trachea wall 26 as shown in FIG. 5. As shown, dilator 15 bends at annular groove 12 which is sufficiently flexible when needle 11 has been withdrawn into dilator to prevent damage to wall 26.

Dilator 15 and breathing tube 20 are positioned within the trachea 31 as shown in FIG. 5. Outer tube 20 is inserted into the trachea until stop member 23 is positioned against the outer membrane 27. Thereafter, dilator 15 is removed by pulling on annular flange 18, FIG. 6.

In another embodiment, guide wire 29 is inserted through needle 11 into the trachea. The guide wire 29 can be used to assist in guiding dilator 15 and tube 20 into the trachea. Guide wire 29 is preferable of the type traditionally known to the art and includes a coating thereover such as a Teflon ® or like coating. Guide wire 29 is attached to annular flange 18 and enters fitting 12 through opening 28 and is found in the shape of a loop. Preferably a small seal 28a, comprising an epoxy material, is placed over the opening and wire. Because of the coating on traditional guide wires, it is possible to "slide" guide wire 29 through the hardened seal 28a and opening 28 but prevents any air leakage. The guide wire is inserted coaxially through needle 11 and into lumen 31. Dilator 15 and tube 20 will follow guide wire 29 as it is inserted into lumen 31.

While a presently preferred embodiment of the invention has been shown and described in particularity, the invention may be otherwise embodied within the scope of the present claims.

What is claimed is:

1. A percutaneous device for performing tracheostomies or cricothyroidectomies comprising:
   a. a hollow needle having a sharp distal end and adapted for connection to syringe means at its other end;
   b. a flexible dilator slidably positioned coaxially over said needle, said dilator having a conical portion having an annular groove adjacent the larger end of said conical portion, the apex of said conical portion being positioned adjacent said distal end of said needle, and said conical portion terminating at said annular groove; and
   c. a flexible breathing tube slidably positioned coaxially over said dilator for insertion into a trachea or larynx.

2. A percutaneous device as set forth in claim 1 wherein the height of the conical portion of the dilator is about one-half the diameter of trachea or larynx.

3. A percutaneous device as set forth in claim 1 or 2 wherein said dilator includes an annular flange at its proximate end.

4. A percutaneous device as set forth in claim 1 or 2 wherein said breathing tube includes stop means.

5. A percutaneous device as set forth in claim 1 or 2 wherein said needle includes an opening for insertion of a guide wire therethrough.

6. A percutaneous device as set forth in claim 5 including a guide wire positioned through said opening in said needle.

* * * * *